United States Patent [19]

Bogdanovic

[11] 4,301,081

[45] Nov. 17, 1981

[54] ALKALI METAL COMPLEX COMPOUNDS

[75] Inventor: Borislav Bogdanovic, Mülheim an der Ruhr, Fed. Rep. of Germany

[73] Assignee: Studiengesellschaft Kohle mbH, Mülheim an der Ruhr, Fed. Rep. of Germany

[21] Appl. No.: 115,595

[22] Filed: Jan. 28, 1980

Related U.S. Application Data

[62] Division of Ser. No. 905,489, May 12, 1978, Pat. No. 4,229,354.

[30] Foreign Application Priority Data

May 17, 1977 [DE] Fed. Rep. of Germany ....... 2722221

[51] Int. Cl.$^3$ .......................................... C07D 307/06
[52] U.S. Cl. ........................... 260/347.2; 260/346.11; 260/347.7; 260/347.8; 564/305; 564/500; 564/502; 564/511; 568/20; 568/63; 568/325; 568/328; 568/329; 568/336; 568/367; 568/376; 568/415; 568/420; 568/442; 568/497

[58] Field of Search ............. 260/346.11, 347.2, 347.3, 260/347.7, 347.8; 568/20, 63, 325, 328, 329, 336, 367, 376, 415, 420, 442, 497; 564/511, 305, 500, 502

[56] References Cited

PUBLICATIONS

Miles et al., Journal of Organic Chemistry, vol. 30 (1965) pp. 1007–1011.
Dingwall et al., Chemical Communications, 1969, p. 466.

*Primary Examiner*—Richard Raymond
*Attorney, Agent, or Firm*—Sprung, Felfe, Horn, Lynch & Kramer

[57] ABSTRACT

The invention includes novel alkali metal complex compounds (and processes for their preparation) which are useful, inter alia for the hydrogenation of alkali metals at room temperature or below room temperature to form hydrides or nitrides.

10 Claims, No Drawings

ALKALI METAL COMPLEX COMPOUNDS

This is a division of application Ser. No. 905,489, filed May 12, 1978, now U.S. Pat. No. 4,229,354.

BACKGROUND

The present invention relates to a method of preparing alkali metal hydrides and nitrides by means of easily accessible, new alkali metal complex compounds as well as said new alkali metal complex compounds and their preparation.

Alkali metal hydrides, such as for example lithium hydride or sodium hydride, are formed, as it is known, from the elements lithium and hydrogen at temperatures above 300° C., and especially at temperatures around 700° C. (Kirk-Othmer 1967, Vol. 12, p. 544; Ullmann, Vol. 8, 1957, p. 723). At room temperature, hydrogen does not react with lithium, and is not absorbed by metal no matter how finely divided (E. Wiberg and E. Amberger, "Hydrides of the Elements of Main Groups I–IV", Elsevier Publishing Co., 1971, p. 19).

In the presence of catalysts such as tungsten (IV) or molybdenum (IV) sulfide, the temperature for the preparation of lithium hydride, for example, can be reduced to 310° to 345° C., and in the presence of lithium stearate as catalyst, it can be reduced to from 240° to 330° C. For the preparation of sodium hydride, catalysts of sodium stearate are used. At a temperature of less than 200° C., it has not been possible to prepare lithium hydride to date. The lowest temperature yet given for the preparation of potassium hydride is 140° C. (Methodicum Chim., Vol. 7, pp. 10–12).

The preparation of lithium nitride at temperatures lower than 350° C., even under the influence of catalysts, has never been described. Temperatures between 500° and 800° C. are preferred (op. cit., p. 60).

THE INVENTION

Surprisingly, it has been found that the hydrogenation of alkali metals can be performed easily if the reaction is preformed in the presence of suitable alkali metal complex compounds as catalyst. The formation of the hydrides and nitrides then takes place at room temperature or lower (+25 to −100° C.). The absorption of hydrogen or nitrogen, as the case may be, takes place at standard pressure or in a slight vacuum, so that the use of excess hydrogen or nitrogen pressure is possible, but usually is not necessary.

It is desirable to perform the hydrogenation or nitridation by mixing the catalyst in dissolved form and the alkali metal in the form of a fine sand, so as to filter off the insoluble reaction products such as lithium hydride or sodium hydride after the end of the reaction.

The alkali metal complex compounds used as catalysts contain several metal atoms per molecule, and can be represented by the General Formulas I and II:

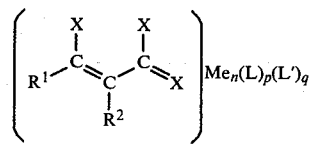

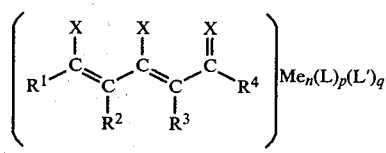

wherein Me represents an alkali metal, X sulfur or oxygen, n a whole number from 3 to 20, L and L' are each mono or polyfunctional ethers or amines, p and q are whole numbers from 0 to 4, $R^1$, $R^2$, $R^3$ and $R^4$ hydrogen, alkyl, cycloalkyl, aralkyl or aryl moieties, and/or two or more such moieties closed to form an aliphatic or aromatic mono- or polycyclic ring system (preferably not all of the $R^1$, $R^2$, $R^3$ and $R^4$ are hydrogen). Compounds of these types are obtained by the reaction of the compounds represented by Formulas III to VII with alkali metals in the presence of the above-named ethers or amines wherein each of $R^1$, $R^2$, $R^3$ and $R^4$ and X is defined as above.

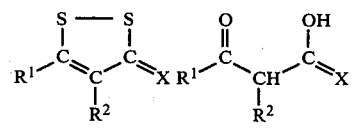

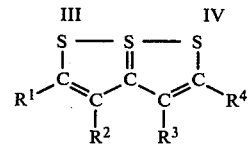

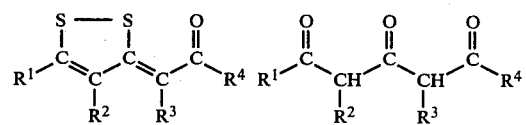

Soluble alkali metal complex compounds are formed which contain more than two alkali metal atoms per molecule.

In the definition given above for $R^1$, $R^2$, $R^3$ and $R^4$, alkyl preferably contains 1 to 12 (particularly 1 to 6) carbon atoms; cycloalkyl preferably contains 3 to 8, (particularly 5 to 6) ring members; aralkyl preferably contains 1 to 12 (particularly 1 to 6 and more particularly 1 to 2) carbon atoms in the alkyl portion and is preferably mono- or bi-cyclic carbocyclic in the aryl portion to include in the aryl portion e.g. phenyl, naphthyl and biphenyl; aryl is defined as shown above for the aryl portion of aralkyl moieties. In case that such moieties are closed to form an aliphatic or aromatic mono- or polycyclic ringsystem, rings are preferably between $R^1$ and $R^2$ or $R^2$ and $R^3$ and $R^4$ and are preferably aromatic rings. Preferred polycyclic ringsystems contain rings between $R^1$ and $R^2$, as well as additionally between $R^3$ and $R^4$.

Nothing is known in the literature concerning the alkali metal compounds of Formulas I or II with n=3 or more which can be made by the present method. In two cases mention is made of compounds of type II with n=2 as intermediates, namely a disodium salt of pentane-1,3,5-trithion (II, X=S, $R^1$, $R^2$, $R^3$, $R^4$=H, Me=Na, n=2) in the synthesis of 1,6,6a-trithiopentalene (V, $R^1$, $R^2$, $R^3$, $R^4$=H) I. G. Dingwall, D. H. Reid, I. D. Symon, Chem. Comm. 466 (1969)), and disodium salts of 1,3,5-triketones (II, X=O, Me=Na, n=2) in the preparation of the corresponding 1,3,5-triketones (VII) (M. L. Miles et al., J. Org. Chem., 30, 1007 (1965)).

The number of alkali metal atoms in the alkali metal complexes which can be prepared by the present method depends to some extent on the structure of the compound III to VII that is used in each case or on the nature of their substituents, on the alkali metal, on the ether or amine that is used, and on the conditions of the reaction. For example, 1,2,-dithiol-3-thione (III, X=S, $R^1$, $R^2$=H) with lithium in THF at 0° C. reacts to produce a dilithium derivative, while in the reaction of 4-phenyl-1,2-dithiol-3-thion (III, X=S, $R^1$=H, $R^2$=$C_6H_5$) with lithium under the same reaction conditions a lithium complex is obtained having seven lithium atoms per molecule. Benzo-1,2-dithiol-3-one (III, X=O, $R^1$, $R^2$=—(CH=CH)$_2$—) reacts with lithium in tetrahydrofuran at 0° C. to form a dilithium derivative; if instead of benzo-1,2-dithiol-3-one, the corresponding thio compound (III, X=S, $R^1$, $R^2$=—(CH=CH)$_2$—) is used, under the same reaction conditions with lithium, a complex is obtained having six lithium atoms and with sodium, a complex having four sodium atoms.

The number of alkali metal atoms in alkali metal complexes I and II is generally very much greater than two when compounds III to VIII with phenyl groups as substituents are used. For example, 2,4-diphenyl-1,6,6a-trithiapentalene (V, $R^1$, $R^3$=$C_6H_5$, $R^2$, $R^4$=H) at 0° C. reacts in tetrahydrofuran with lithium or with sodium to form complexes containing ten alkali metal atoms; a complex which also contains ten lithium atoms per molecule is obtained under the same conditions from 1,5-diphenylpentane-1,3,5-trione (VII, $R^1$, $R^4$=$C_6H_5$, $R^2$, $R^3$=H) and lithium in monoglyme.

The alkali metal complexes which can be made by the present method having more than two alkali metal atoms, are highly reactive organometallic compounds which are sensitive to air and moisture, so that their preparation must be performed in an inert gas atmosphere. The alkali metal complexes which can be prepared by this method can be obtained in solution and put to use in dissolved form, and they can also be used in solid, finely divided form in the catalysis.

The claimed alkali metal complexes containing several alkali metal atoms per molecule can be used either as such or in combination with transition metal compounds, for example, for the preparation of alkali metal hydrides, the fixing of molecular nitrogen, and as hydrogenation catalysts.

EXAMPLES

EXAMPLE 1

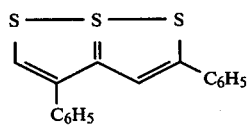
(1)

1.49 g (214 mAtom) of lithium sand was added to a solution of 3.73 g (12.0 nMol) 2,4-diphenyl-1,6,6a-trithiapentalene (1) in 200 ml of absolute tetrahydrofuran (THF), and the mixture was stirred for 18 hours at 0° C. Then the dark violet to black solution was separated from the unreacted lithium sand by filtration at 0° C. By the degradation of an aliquot part (2.0 ml) of this solution with water and acidimetric lithium determination it was found that 9.81 gram atoms of lithium reacted with one mole of substance (1), corresponding to a transformation of 98% of the starting substance (1) to the lithium complex named below. For the isolation of the lithium complex in solid form, 500 ml of pentane was added to the THF solution at 0° C. with stirring, and the mixture was allowed to stand for two hours. Then the black suspension was filtered at 0° C. and the residue was washed with pentane and vacuum dried ($10^{-4}$ Torr) at 20° C. to constant weight. 4.96 g (91.4%) was obtained of the highly air-sensitive complex:

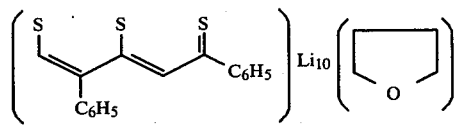

$C_{21}H_{20}S_3OLi_{10}$ (mol. wt.=453.4) calc.:C:55.63; H:4.45; S:21.19; Li:15.32%;
found: C:55.22; H:4.65; S:21.13; Li:15.10%.

The complex isolated in solid form is soluble in THF and can be re-precipitated with the same composition by the addition of pentane to the THF solution.

EXAMPLE 2

In a manner similar to Example 1, 1.06 g (3.36 mMol) of 2,4-diphenyl-1,6,6a-trithiapentalene (1) was reacted with 0.57 g (82.2 mAtom) of lithium sand in 50 ml of THF at 0° C. After 5 hours of reaction, the solution was separated from the unreacted lithium sand, and it was determined by hydrolysis of the excess lithium that 9.7 gram atoms of lithium had reacted with one mole of substance (1), corresponding to a transformation of the latter to its decalithium complex compound of 97%. To isolate the decalithium complex as a 1,2-dimethoxyethane adduct, the solution was concentrated in vacuo (0.2–0.3 Torr) to 25 ml, and 20 ml of 1,2-dimethoxyethane was added, whereupon a black precipitate formed. The suspension was let stand for 3 h at 0° C., the precipitate was filtered from the dark-colored solution, and the precipitate was vacuum dried (20° C., $10^{-4}$ Torr) to constant weight. 0.82 g (51.5%) was obtained of the highly air-sensitive complex compound:

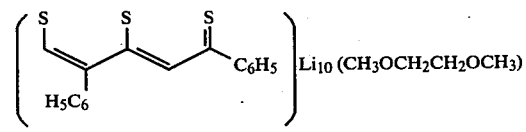

$C_{21}H_{22}S_3O_2Li_{10}$; (mol. wt.=471.5);
calc. C:53.4; H:4.70; Li:14.70%;
found C:53.0; H:4.80; Li:14.67%.

By the addition of 40 ml of 1,2-dimethoxyethane to the mother liquor, an additional 0.27 g (17% of the theory) of the same complex (calc. 14.70% Li, found 14.50% Li) was isolated, so that the total yield of the isolated complex amounts to 1.09 g or 68.5% of the theory.

EXAMPLE 3

In a manner similar to Example 1, 1.98 g (6.33 mMol) of 2,4-diphenyl-1,6,6a-trithiapentalene (1) was reacted with 3.59 g (156 mAtom) of sodium sand in 60 ml of THF at 0° C. After 21 hours of reaction time, the dark violet solution of the sodium complex was filtered from the unreacted sodium sand at 0° C. By the degradation of an aliquot part of this solution with water and acidimetric determination of the sodium, it was found that 9.98 gram atoms of sodium had reacted with one mole of 2,4-diphenyl-1,6,6a-trithiapentalene (1), corresponding to a virtually quantitative transformation of the starting compound (1) to the decasodium complex of the latter. By the addition of 120 ml of 1,2-dimethoxyethane to the THF solution, the decasodium complex was isolated in solid form in a yield of 2.30 g (57.5% of the theory), in the manner described in Example 2, as a 1:1 addition product with 1,2-dimethoxyethane:

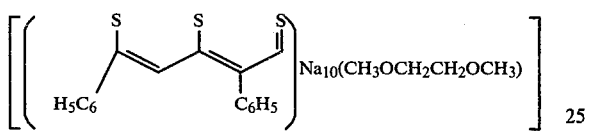

$C_{21}H_{22}S_3O_2Na$; (mol. wt.=632.4); calc.:36.4% Na, found:36.25% Na.

EXAMPLE 4

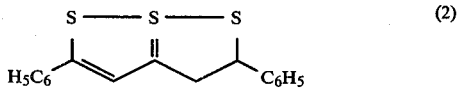 (2)

In a manner similar to Example 1, 2.15 g (6.90 mMol) of 2,5-diphenyl-1,6,6a-trithiapentalene (2) was reacted with 1.25 g (179 mAtom) of lithium sand in 50 ml of THF at 0° C. After 16 hours of stirring the reaction mixture at 0° C., the dark violet solution was separated from the unreacted lithium sand. By hydrolysis of an aliquot part of the solution and acidimetric determination of the lithium, a virtually quantative transformation of compound (2) to its decalithium complex was found (10.2 gram atoms of lithium had been transformed per mole of compound (2)). By the addition of 200 ml of pentane to the THF solution, the decalithium complex was obtained in the form of its 1:1 adduct with THF:

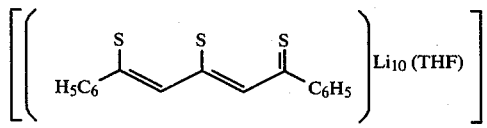

in a yield of 2.84 g (90.8% of the theory) in solid form.
$C_{21}H_{20}S_3OLi_{10}$; mol. wt. 453.4; calc.:15.30% Li; found:15.56% Li.

The hydrolysis and deuterolysis (Equation 1) of this complex compound can serve for its chemical characterization. The hydrolysis of the complex in solid form (as the THF adduct) or in THF solution yields lithium hydroxide, lithium sulfide (80% yield with respect to the sulfur bound in the complex) plus a mixture of $C_{17}$ hydrocarbons consisting of isomers of 1,5-diphenyl-1,3-pentadiene and a small amount of 1,5-di-phenylpentenes (total yield of $C_{17}$ hydrocarbons, approximately 70% of the theory). In the deuterolysis of the complex, accordingly, tetra-deutero-1,5-diphenyl-1,3-pentadienes are obtained and a small amount of hexadeutero-1,5-diphenylpentenes.

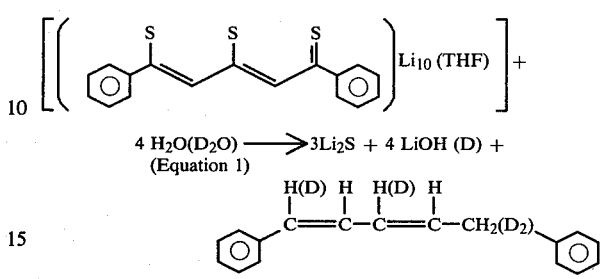

(Equation 1)

The hydrolysis reaction and deuterolysis reaction can be considered as proof of the constitution of the hydrocarbon structure that is the basis of the complex. The decalithium-2,5-diphenyl-1,6,6a-trithiapentalene complex is also characterized by its absorption bands in the ultraviolet spectrum at 580 nm, $\epsilon = 11,000$ (as $5 \cdot 10^{-4}$ molar THF solution).

EXAMPLE 5

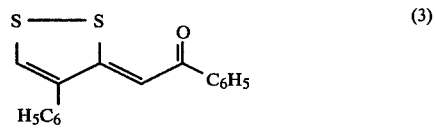 (3)

In a manner similar to Example 1, 0.84 g (2.84 mMol) of α-(4-phenyl-1,2-dithiol-3-ylidene)-acetophenone (3) is reacted with 0.51 g (73 mAtom) of lithium sand in 60 ml of THF at 0° C. After 18 hours of reaction at 0° C, the dark violet solution of the lithium complex is separated from the excess lithium by filtration at 0° C. On the basis of acidimetric determination of the lithium in the solution, 10.1 gram atoms of lithium had reacted with one mole of compound (3) to form a decalithium complex thereof.

EXAMPLE 6

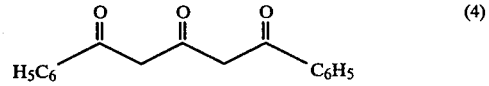 (4)

14.3 g (2.06 moles) of lithium sand was added to a solution of 9.46 g (35.6 mMol) of 1,5-diphenylpentane-1,3,5-trione (4) in 450 ml of absolute THF, and the mixture was stirred at 0° C., the solution assuming a dark blue-violet color after about 24 hours. After 40 hours of reaction, the solution was filtered off from the excess lithium sand, and by the hydrolysis of an aliquot part of the solution and acidimetric determination of the lithium it was found that 10.06 gram atoms of lithium had reacted with one mole of the triketone (4); this corresponds to a quantitative transformation of the triketone to the decalithium complex of compound (4). To isolate the complex in solid form, the solution was concentrated in vacuo to 200 ml, 400 ml of tetramethylethylenediamine ($Me_2NCH_2CH_2NMe_2$) was added, and the mixture was stirred for 2 hours at 0° C. By filtration and drying in a high vacuum, the decalithium complex of the triketone (4) was obtained in solid form, in a yield of 8.50 g (40% of the theory), as an adduct with one mole of tetramethylethylenediamine and two moles of THF:

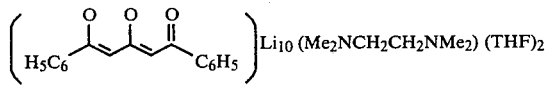

C₃H₄₄N₂O₅Li₁₀ mol. wt.=595.4;
calculated: 4.70% N; 1.66% Li;
found: 4.72% N; 11.48% Li.

EXAMPLE 7

6.41 g (0.92 gram atoms) of lithium sand was added to a solution of 3.61 g (13.6 mMol) of 1,5-diphenylpentane-1,3,5-trione (4), in 115 ml of absolute 1,2-dimethoxyethane (CH₃OCH₂—CH₂OCH₃) and the mixture was stirred at 0° C. The course of the reaction was followed by taking 5.0 ml samples of the suspension at various intervals of time, filtering the excess lithium sand from the samples, degrading the filtrate with water, and titrating it with 0.1N HCl. After 2, 27 and 48 hours, respectively of reaction time, a lithium concentration was found in the solution corresponding to 7.9, 9.8 and 10.3 gram atoms, respectively, of lithium per mole of compound (4). This corresponds to a quantitative transformation of the triketone (4) to its decalithium complex, 1,2-dimethoxyethane having been used instead of THF as the reaction medium in this example.

EXAMPLE 8

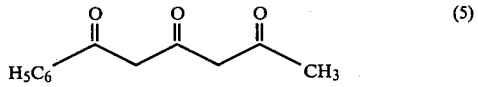

In a manner similar to Example 1, 2.02 g (9.9 mMol) of 6-phenylhexane-2,4,6-trione (5) was reacted with 2.85 g (0.41 gram atoms) of lithium sand in 75 ml of THF at 0° C. After 50 hours of reaction time, the excess lithium sand was filtered from the solution and it was found as described in Example 1 that 5.1 gram atoms of lithium had reacted with one mole of the triketone (5), corresponding to a quantitative transformation of the triketone (5) to a pentalithium complex. To isolate the complex, the solution was concentrated in vacuo to 15 ml, 35 ml of tetramethylethylenediamine was added at 0° C., and then the solution was concentrated in vacuo to 30 ml. The suspension thus obtained was stirred for 2 hours at 0° C., filtered, and the residue was dried in a high vacuum. 2.05 g (56% of the theory) of a complex was obtained having the following composition:

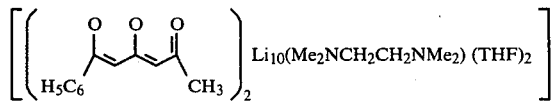

C₃₈H₆₀C₈N₂Li₁₀ (mol. wt. =737.4);
calculated: 3.80% N, 9.41% Li,
found: 3.81% N, 9.18% Li.

EXAMPLE 9

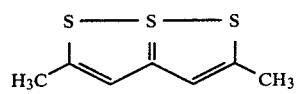

In a manner similar to Example 1, 1.05 g (5.58 mMol) of 2,5-dimethyl-1,6,6a-trithiapentalene (6) was reacted with 0.72 g (103 mAtom) of lithium sand in 30 ml of THF at 0° C. After 3 hours of reaction, it was found by the method described in Example 1 that 4.0 gram atoms of lithium had reacted with one mole of compound (6) and, after an additional five hours of stirring the reaction mixture at 0° C., the lithium concentration in the solution remained virtually constant. Accordingly, a tetralithium complex of compound (6) is formed in THF solution at 0° C.

EXAMPLE 10

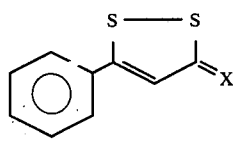

In a manner similar to Example 1, 0.27 g (1.3 mMol) of 5-phenyl-1,2-dithiol-3-thione (7) was reacted with 0.27 g (38 mAtom) of lithium sand in 50 ml of THF at 0° C. At different intervals of time, 5.0 ml samples of the suspension were taken and filtered, water and excess 0.1N HCl were added to the filtrate, and the filtrate was titrated back with 0.1N NaOH. After 3 hours of reaction it was found that 7.04 gram atoms of lithium had reacted per mole of compound (7) and over the next few hours the lithium concentration in the solution remained virtually constant. Accordingly, a heptalithium complex of compound (7) had been formed from the latter and lithium in THF at 0° C.

For the isolation of the complex in solid form, the excess lithium was filtered from the solution, 33 ml of tetramethylenediamine is added, and the mixture is concentrated in vacuo to 40 ml. By filtration and drying the precipitate in a high vacuum, 0.38 g (66% of the theory) of the heptalithium complex compound of (7) is obtained in the form of its 1:1 adduct with tetramethylethylenediamine and THF:

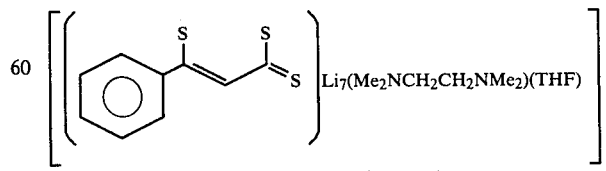

C₁₉H₃₁S₃N₂OLi₇ (mol. wt.=448.2);
calculated: 6.27% N; 10.9% Li;
found: 5.96% N; 11.4% Li.

EXAMPLE 11

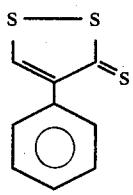 (8)

In a manner similar to Example 1, 0.57 g (2.73 mMol) of 4-penyl-1,2-dithiol-3-thiene (8) was reached with 2.34 g (102 mAtom) of sodium sand in 100 ml of THF at 0° C. As in Example 10, the course of the reaction was pursued by taking samples (15.0 ml) and by acidimetric determination of the sodium in the samples. The course of the reaction is indicated by the following table:

| Reaction time in hours | Grams atoms of Na per mole of compound (8) | Color of the solution |
|---|---|---|
| 24 | 0.81 | brown |
| 28 | 1.77 | dark brown |
| 52 | 5.75 | dark blue |
| 90 | 6.78 | dark violet |
| 180 | 7.27 | dark violet |

Accordingly, a heptasodium complex of compound (8) forms from the latter and sodium in THF at 0° C.

EXAMPLE 12

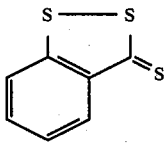 (9)

In a manner similar to Example 1, 1.50 g (8.2 mMol) of benzo-1,2-dithiol-3-thione (9) was reacted with 0.82 g (117 mAtom) of lithium sand in 180 ml of THF at 0° C. After 2 hours of reaction, a lithium concentration was found in the solution corresponding to 6.2 gram atoms of lithium per gram-molecule of benzo-1,2-dithiol-3-thione, and after an additional 24 hours of reaction, 6.1 gram atoms of lithium per gram-molecule of benzo-1,2dithiol-3-thione. By the addition of 250 ml of pentane to the THF solution, the hexalithium-benzo-1,2-dithiol-3-thione complex was isolated in solid form, in a yield of 1.22 g (50% of the theory) in the form of a monotetrahydrofuran adduct:

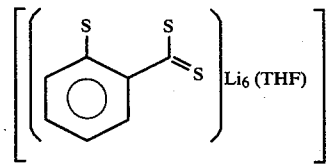

$C_{11}H_{12}S_3OLi_6$ (mol. wt. = 298); calc. 14.1% Li, found 13.9% Li.

EXAMPLE 13

In a manner similar to Example 1, 0.74 g (4.0 mMol) of benzo-1,2-dithiol-3-thione (9) was reacted with 0.85 g (37 mAtom) of sodium sand in 70 ml of THF at 0° C. After 48 hours of reaction at 0° C., a sodium concentration was found in the solution corresponding to 4.0 gram atoms of Na per gram-molecule of benzo-1,2-dithiol3-thione. Accordingly, a tetrasodium complex of compound (9) is formed from compound (9) and sodium in THF at 0° C.

EXAMPLE 14

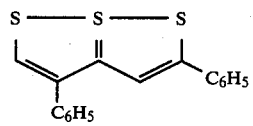 (1)

2.70 g (69.0 mAtom) of metallic potassium is added portion-wise at 0° C. to a solution of 1.04 g (3.33 mMol) of 2,4-diphenyl-1,6,6a-trithiapentalene (1) in 50 ml of absolute tetrahydrofuran (THF). The mixture is stirred for 48 hours at 0° C. After this time the metallic potassium is separated from the solution and reweighed. The potassium weight loss of 0.43 g corresponded to a reaction of 3.3 gram atoms of potassium with one mole of compound (1). Potassium (2.27 g) was again added to the solution which was stirred for 17 hours at room temperature. The degradation of an aliquot amount of the solution with water and the acidimetric determination of the potassium indicated a molar ratio of K: (1) of 3.9:1.0. The solution was stirred for another 93 hours in the presence of potassium, and the potassium complex separated in the form of a black precipitate. By filtering the precipitate and drying it in a high vacuum to constant weight, 1.59 g of the complex was obtained (yield 88%).

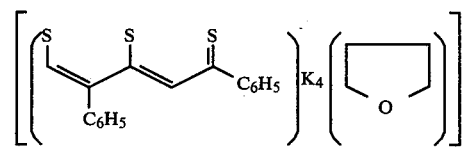

$C_{21}H_{20}S_3OK_4$ (mol. wt. = 540.5); calculated: 28.9% K; found: 29.8% K.

EXAMPLE 15

The use of the benzo-1,2-dithiol-3-thione hexalithium complex compound of Example 12 as a catalyst for the hydrogenation of lithium to lithium hydride 1.0 gram (143 mAtom) of lithium sand was added to a solution of 2.24 mMol of benzo-1,2-dithiol-3-thionehexalithium in 90 ml of THF (prepared as described in Example 12), with stirring, at 0° C., in a hydrogen gas atmosphere (standard pressure), whereupon a slow, uniform absorption of hydrogen began. The stirring of the reaction mixture at 0° C. in hydrogen gas atmosphere was continued to the end of the hydrogen absorption 92 hours later, when it was determined that a total of 730 ml of hydrogen gas at 20° C. had been absorbed. The lithium hydride that had precipitated by this time was separated from the catalyst solution and identified by infrared spectroscopy. The amount of hydrogen absorbed corresponded to a transformation of 43% of the lithium to lithium hydride, signifiying also that 28 moles of lithium hydride had been formed per mole of catalyst.

EXAMPLE 16

Use of the benzo-1,2-dithiol-3-thione-hexalithium complex of Example 12, in combination with FeCl$_3$ (molar ratio of Li complex : FeCl$_3$ = 6:1) as a catalyst for the hydrogenation of lithium to lithium hydride 0.068 g (0.4 mMol) of FeCl$_3$ (in solid form) was added to a solution of 2.40 mMol of benzo-1,2-dithiol-3-thionehexalithium in 80 ml of THF (prepared as described in Example 12), with stirring, at −30° C., and the mixture was stirred for one-half hour at −30° C. After that, 1.0 g (143 milliatoms) of lithium sand was added to the catalyst solution at 0° C. in a hydrogen gas atmosphere (standard pressure), with stirring, whereupon a uniform absorption of hydrogen began. After 94 hours the hydrogen absorption virtually ceased, and a voluminous precipitate of lithium hydride had formed. The amount of hydrogen gas absorbed (1740 ml of H$_2$ of 20° C./760 Torr) corresponded to a transformation of 101% of the input lithium to lithium hydride, and signifies that 60 moles of lithium hydride had formed per mole of the catalyst.

In a comparative test it was shown that, under the same conditions, but in the absence of the benzo-1,2-dithiol-3-thione hexalithium complex compound, lithium sand is virtually unattacked by hydrogen, with or without the addition of FeCl$_3$.

EXAMPLE 17

Use of 2,4-diphenyl-1,6,6a-trithiapentalene-sodium complex of Example 3 in combination with FeCl$_3$ (molar ratio of the sodium complex to FeCL$_3$ = 6:1), as catalyst for the hydrogenation of sodium to sodium hydride 1.30 g (4.15 mMol) of 2,4-diphenyl-1,6,6a-trithiapentalene (1) was dissolved in 40 ml of THF, 2.73 g (118.7 mAtom) of sodium sand was added to the solution, and the mixture was stirred for 20 hours at 0° C. Then the excess sodium sand was filtered from the solution, and an aliquot portion of the filtrate was treated with H$_2$O and the acidimetric determination of the sodium showed a molar ratio of sodium to compound (1) of 9.2:1.0.

To the remaining solution containing 3.46 mMol of the trithiapentalene-sodium complex, 1.34 g (58.1 mAtom) of sodium sand was added, with stirring, at 0° C. in a hydrogen gas atmosphere (standard pressure, whereupon a very slow absorption of H$_2$ began (in 76 hours 43 ml of H$_2$ was absorbed). Then 0.094 g (0.58 millimole) of FeCl$_3$ in 10 ml of THF was added to the suspension, and the mixture was again stirred in a hydrogen atmosphere at 0° C., while a uniform hydrogen absorption began. By the end of the hydrogen absorption 67 hours later, a total of 557 ml of H$_2$ of 20° C. had been absorbed, corresponding to a transformation of about 80% of the input sodium to sodium hydride (13 to 14 catalytic steps to one mole of catalyst).

EXAMPLE 18

(In this example, the 2,4-diphenyl-1,6,6a-trithiapentalene-sodium complex was prepared in situ, in the presence of FeCl$_3$. As in Example 17, the catalytic combination was used for the hydrogenation of sodium to sodium hydride.)

3.73 g (162 mAtom) of sodium sand was added, with stirring, to a solution of 0.57 g (1.79 mMol) of 2,4-diphenyl-1,6,6a-trithiapentalene (1) and 0.56 g (3.58 mMol) of FeCl$_3$ in 50 ml of THF, at 0° C. in a hydrogen gas atmosphere (standard pressure), whereupon a uniform absorption of hydrogen began. By the end of the hydrogen absorption, a total of 1430 ml of H$_2$ of 20° C. and 760 Torr had been absorbed within 62 hours at uniform temperature and constant rate of stirring, corresponding to a transformation of 74% of the input sodium to sodium hydride, and to a catalytic formation of 66 moles of sodium hydride to a mole of the catalyst.

EXAMPLE 19

Benzo-1,2-dithiol-3-thione-hexalithium complex of Example 12 as catalyst for the fixation of molecular nitrogen 1.28 g (183 mAtom) of lithium sand was suspended in 80 ml of THF and the suspension was stirred magnetically at a rate of 40 rpm at 0° C. and in a nitrogen gas atmosphere at standard pressure; within 24 hours a nitrogen absorption of 18 ml N$_2$ (of 20° C.) was found. Then, at the same stirring speed and temperature, 0.30 g (1.63 mmol) of benzo-1,2-dithiol-3-thione was added to the lithium sand suspension in a nitrogen gas atmosphere; after a few hours (in which time the benzo-1,2-dithiol-3-thione-hexalithium complex formed as in Example 12) the nitrogen absorption became considerably more rapid. From the time of the addition of the benzo-1,2-dithiol-3-thione to the end of the nitrogen absorption, amounting to about 130 hours, a total of 300 ml of N$_2$ of 20° C. had been absorbed, corresponding to a transformation of 41% of the input lithium to lithium nitride. In this time, 15 moles of Li$_3$N has formed per mole of the benzo-1,2-dithiol-3-thione-hexalithium catalyst. The hydrolysis of the lithium nitride yielded 95 to 100% of the theoretical amount of ammonia.

EXAMPLE 20

Benzo-1,2-dithiol-3-thione-hexalithium complex of Example 12 in combination with FeCl$_3$ (molar ratio of the Li complex to FeCl$_3$ = 6:1) as a catalyst for the fixation of molecular nitrogen To a freshly prepared solution of 2.15 mMol of the benzo-1,2-dithiol-3-thione-hexalithium complex compound of Example 12 in 60 ml of THF, 0.058 g (0.36 mMol) of FeCl$_3$ (in solid form) was added at −40° C., with stirring, and the mixture was stirred for 1 h at −40° C. Then 1.3 g (185 mAtom) of lithium sand was added to this solution, with stirring, at 0° C., in a nitrogen gas atmosphere (standard pressure), whereupon the absorption of the nitrogen began. By the end of the nitrogen absorption, 426 ml of N$_2$ of 20° C. had been absorbed in 115 h with the temperature remaining the same and at a constant stirring speed; this corresponds to a transformation of 58% of the input lithium to lithium nitride and to a catalytic formation of 16.5 moles of Li$_3$N to one mole of the catalyst, or 98 moles of Li$_3$N to one gram atom of iron. The hydrolysis yielded 88% of the expected amount of ammonia.

EXAMPLE 21

To a solution of 0.40 g (1.28 mMol) of 2,4-diphenyl-1,6,6a-trithiapentalene (1) in 40 ml of THF there was added 0.89 g of a potassium-sodium alloy consisting of 80 wt.-% of K and 20 wt.-% of Na. The mixture was stirred for 67 hours at 20° C., the color of the solution changing from dark red to blackish violet. By the hydrolysis of an aliquot part of the solution and acidimetric determination of the alkali metal it was found that a total of 9 gram atoms of alkali metal had reacted with one mole of compound (1); by means of atomic absorption spectroscopy, the atomic ratio of sodium to potassium in the complex was determined to be 1:2.8.

What is claimed is:

1. An alkali metal complex compound of general formula

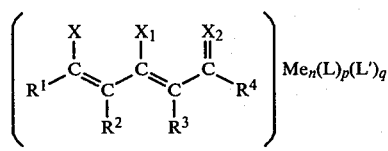 I wherein Me represents an alkali metal, each X represents sulphur or oxygen, with the proviso that (1) all three X atoms are sulfur, (2) all three X atoms are oxygen or (3) X and $X_1$ are sulfur and $X_2$ is oxygen, n represents a whole number from 3 to 20, L and L' represents a mono- or polyfunctional ether or amine, respectively, p and q are whole numbers from 0 to 4, $R^1$, $R^2$, $R^3$, $R^4$ are each hydrogen, alkyl, cycloalkyl, aralkyl or aryl moieties and/or two or more such moieties closed to form an aliphatic or aromatic ring system.

2. An alkali metal complex compound of claim 1 wherein each X represents sulfur or oxygen; two of $R^1$, $R^2$, $R^3$ and $R^4$ are phenyl and the other two are hydrogen.

3. An alkali metal complex compound of claim 2 wherein each X represents sulfur..

4. An alkali metal complex compound of claim 2, wherein X represents oxygen.

5. An alkali metal complex compound of claim 1 wherein the alkali metal is lithium.

6. An alkali metal complex compound of claim 1 wherein L or L' represent tetrahydrofuran.

7. An alkali metal complex compound of claim 1 wherein L or L' represent $C_1$–$C_6$-dialkylene ether of ethylene glycol.

8. A compound of claim 7 wherein $C_1$–$C_6$-dialkylene is dimethylene.

9. An alkali metal complex compound of claim 1 wherein L or L' represent $C_1$–$C_6$-tetraalkyl-$C_1$–$C_6$-alkylene diamine.

10. A compound of claim 9 wherein $C_1$–$C_6$-tetraalkyl is tetramethyl wherein $C_1$–$C_6$-alkylene is ethylene.

* * * * *